United States Patent
Sablone et al.

(10) Patent No.: US 11,554,924 B2
(45) Date of Patent: Jan. 17, 2023

(54) APPARATUS AND METHOD FOR TRANSFERRING ARTICLES

(71) Applicant: Fameccanica.Data S.p.A., San Giovanni Teatino (IT)

(72) Inventors: Gabriele Sablone, San Giovanni Teatino (IT); Carlo Di Sabatino, San Giovanni Teatino (IT); Donato Crisante, San Giovanni Teatino (IT); Massimiliano Rossetti, San Giovanni Teatino (IT)

(73) Assignee: Fameccanica.Data S.p.A.

( * ) Notice: Subject to any disclaimer, the term of this patent is extended or adjusted under 35 U.S.C. 154(b) by 30 days.

(21) Appl. No.: 17/363,201

(22) Filed: Jun. 30, 2021

(65) Prior Publication Data
US 2022/0002097 A1 Jan. 6, 2022

(30) Foreign Application Priority Data

Jul. 1, 2020 (IT) .......................... 102020000015853

(51) Int. Cl.
*B65G 47/86* (2006.01)
*B65G 43/10* (2006.01)
*B65G 54/02* (2006.01)

(52) U.S. Cl.
CPC ........... *B65G 47/847* (2013.01); *B65G 43/10* (2013.01); *B65G 54/02* (2013.01); *B65G 2811/095* (2013.01)

(58) Field of Classification Search
CPC .............. B65G 2811/098; B65G 43/10; B65G 47/847; B65G 54/02

USPC ................................................... 198/375, 379
See application file for complete search history.

(56) References Cited

U.S. PATENT DOCUMENTS 10,167,156 B2 * 1/2019 Ingole ................... B65H 20/12

FOREIGN PATENT DOCUMENTS

| CN | 112203957 A | * | 1/2021 | ....... A61F 13/15764 |
| EP | 0812789 A2 | | 12/1997 | |
| ES | 2913130 T3 | * | 5/2022 | ........... B31B 50/062 |

OTHER PUBLICATIONS

Italian Search Report dated Mar. 15, 2021. 6 pages.

* cited by examiner

*Primary Examiner* — Gene O Crawford
*Assistant Examiner* — Lester Rushin, III
(74) *Attorney, Agent, or Firm* — RMCK Law Group PLC

(57) ABSTRACT

An apparatus and a method for transferring articles from a pick-up area to a delivery area, wherein there is provided a guide element having a guide surface which moves along a closed path at a base speed, and wherein there are provided a plurality of transfer elements, each of which is provided with a gripping surface for holding an article and is movable with respect to the guide surface with a relative speed, so that, with respect to a stationary reference system, each of the transfer elements moves along the closed path with a compound speed given by an algebraic sum of the base speed and the respective relative speed.

10 Claims, 3 Drawing Sheets

APPARATUS AND METHOD FOR TRANSFERRING ARTICLES

CROSS-REFERENCE TO RELATED APPLICATION

This application claims priority to Italian Patent Application No. 102020000015853 filed Jul. 1, 2020. The disclosure of the above application is incorporated herein by reference in its entirety.

TECHNICAL FIELD

The present description relates to an apparatus and a method for transferring articles from a pick-up area to a delivery area.

The invention has been designed specifically in view of the application thereof to machines for manufacturing absorbent sanitary products, for the transfer of components of absorbent sanitary products or of finished absorbent sanitary products from a pick-up area to a delivery area.

In the following description reference will be made to said field of use, but without any limiting purpose.

DESCRIPTION OF THE PRIOR ART

In the machines for manufacturing absorbent sanitary products wide use is made of transfer apparatuses which transfer one or more components of absorbent sanitary articles from a pick-up area to a delivery area. A specific transfer apparatus which is widely used in the machines for manufacturing absorbent sanitary articles is the so-called repitch apparatus, which varies the pitch between articles during the transfer from the pick-up area to the delivery area. In some cases, a repitch apparatus may also perform a rotation of the articles during the transfer from the pick-up area to the delivery area, often in addition to repitching. Such operations are known in the field as "turn and repitch" operations.

The related prior art of repitch apparatuses is quite abundant. For example, document U.S. Pat. No. 4,880,102 shows a device for transferring articles from a first conveyor, whereon articles advance with a first pitch, to a second conveyor, whereon articles advance with a second pitch. The device comprises a plurality of transport elements, which are mounted so as to be rotatable around an axis. During transfer, the speed of the transport elements is varied between the pick-up area and the delivery area.

Substantially similar solutions are known e.g. from U.S. Pat. Nos. 5,480,021, 4,506,779, 4,726,876. Apparatuses varying the article orientation between the pick-up position and the delivery position (turn and repitch operation) are described in U.S. Pat. Nos. 3,728,191 e 4,483,351.

A repitch apparatus must be able to firmly and stably hold the articles on the transport elements during the transfer from the pick-up area to the delivery area. This is normally achieved via a vacuum gripping system, which connects the gripping surfaces of the transport elements to a source of subatmospheric pressure in the path from the pick-up area to the delivery area. EP-A-3336023 describes a repitch apparatus including a plurality of transport elements, which are rotatable independently from one another around an axis and which have respective gripping surfaces provided with suction holes, and a rotating distributor rotatable around said axis independently from the transport elements and having a plurality of suction channels which are connected to the transport elements through pneumatic connection members.

In the field of machines for manufacturing absorbent sanitary articles there is an increasing trend to increase the production speed of the machines. The machines having the best performances which are currently available on the market may reach production speeds amounting to 800-1000 pieces per minute, but it would be desirable to reach production speeds of around 2000 pieces per minute.

One of the problems encountered when increasing the production speed of the machines consists in the constraints in the maximum operating speed of the transfer apparatus.

OBJECT AND SUMMARY OF THE INVENTION

The present invention aims at providing an apparatus and a method for transferring articles from a pick-up area to a delivery area which may increase the operating speed as compared with the solutions according to the prior art.

According to the present invention, said object is achieved thanks to an apparatus and a method having the features set out in claim 1 and claim 8.

The claims are an integral part of the teaching provided herein with reference to the invention.

BRIEF DESCRIPTION OF THE DRAWINGS

The present invention will now be described in detail with reference to the annexed drawings, which are shown by way of non-limiting example only, and wherein.

DETAILED DESCRIPTION

Figure 1:
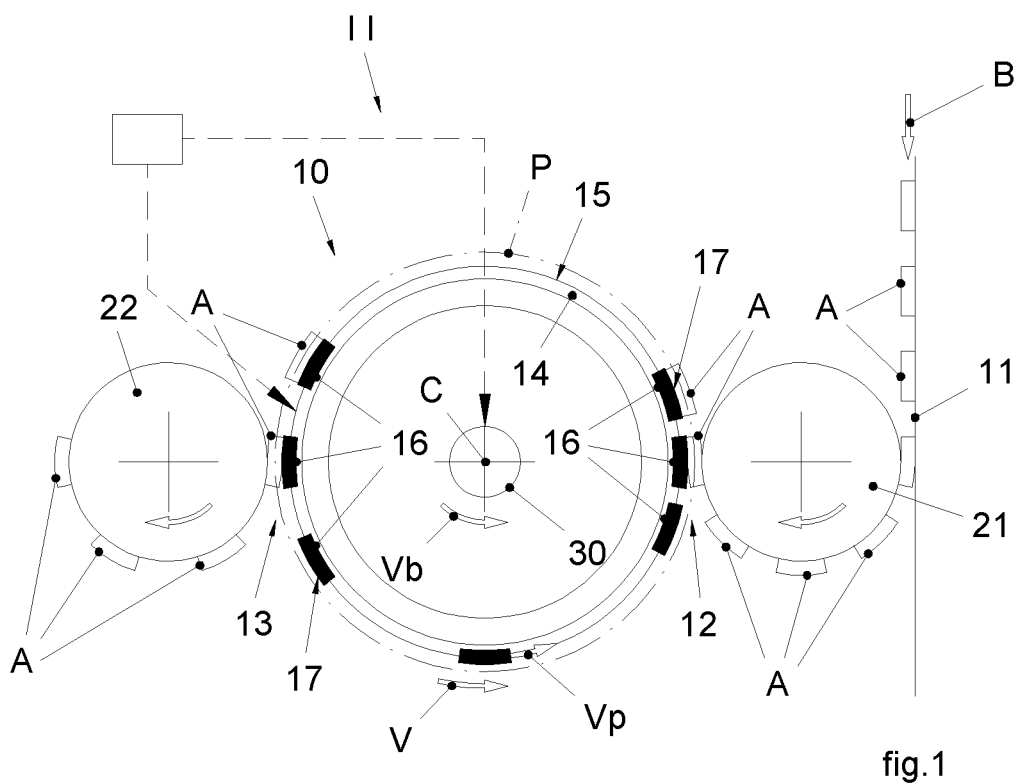
FIG. 1 is a diagrammatic view of a system for transferring articles including a transfer apparatus according to the present invention.
Figure 2:
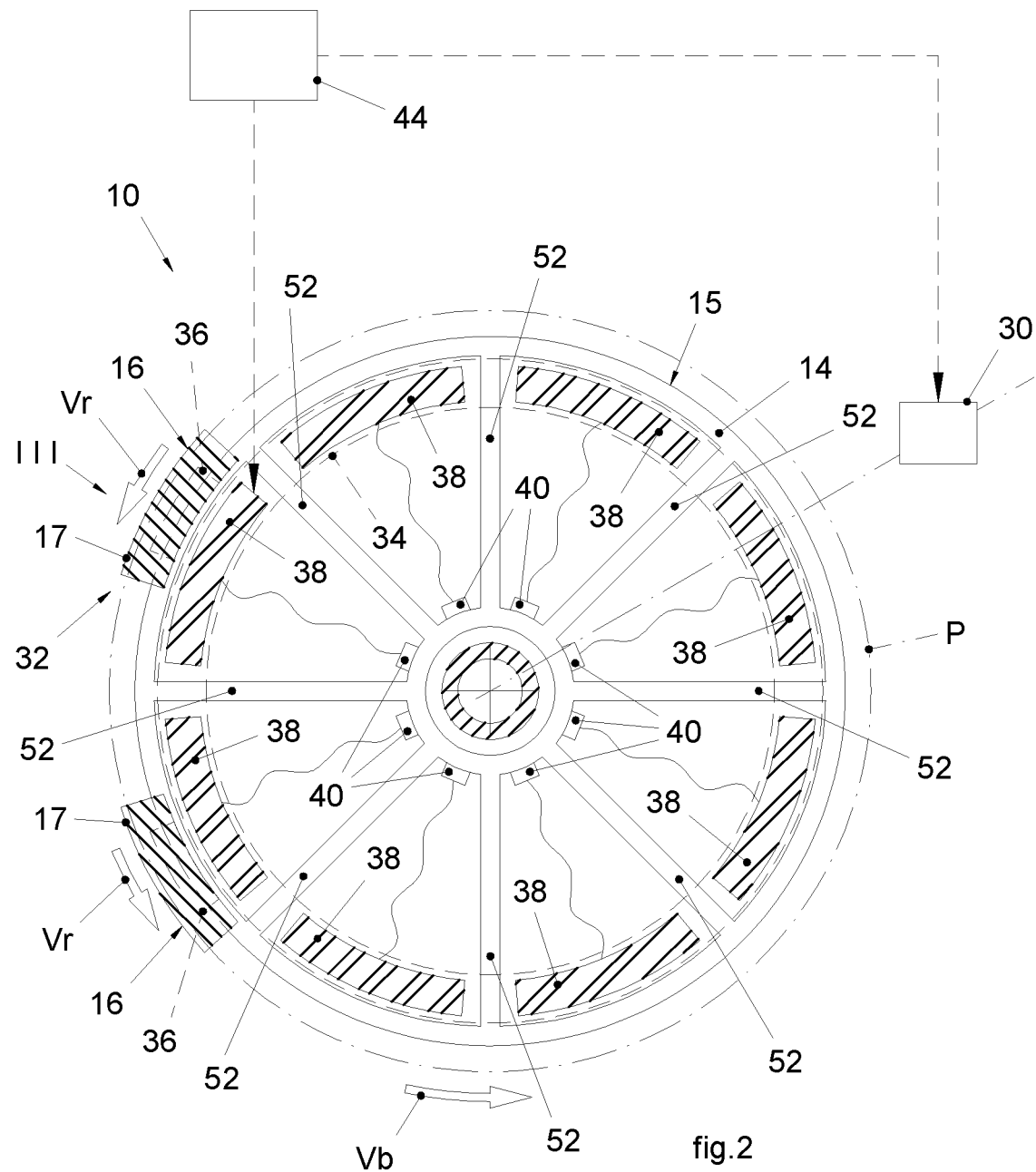
FIG. 2 is a diagrammatic view of the transfer apparatus indicated by arrow II in FIG. 1.

Referring to FIGS. 1 and 2, reference 10 schematically shows a transfer apparatus adapted to perform the transfer of articles A from a pick-up area 12 to a delivery area 13. In a possible embodiment, articles A may be components of absorbent sanitary articles (e.g. side panels, absorbent cores, etc.) or finished or semi-finished absorbent sanitary articles.

In the example schematically shown in FIG. 1, articles A advance along a linear conveyor 11 in the direction shown by arrow B. Articles A are picked up from the linear conveyor 11 by an input wheel 21, which feeds them to the pick-up area 12. The transfer apparatus 10 picks up the articles A on the periphery of the input wheel 21, and transfers them to the delivery area 13, where they are collected by an output wheel 22. In the illustrated example, articles A are spaced from each other by a first pitch in the pick-up area 21, and by a second pitch, which is wider that the first pitch, in the delivery area 13.

Referring to FIGS. 1 and 2, the transfer apparatus 10 includes a guide element 14, having a guide surface 15 extending along a closed path P. The closed path P is schematically shown in FIG. 1 by a dash-and-dot line. In the representation of FIGS. 1 and 2, the closed path P coincides with the guide surface 15. The closed path P extends across the pick-up area 12 and the delivery area 13. In the embodiment shown in FIGS. 1 and 2, the closed path P and the guide surface 15 have a circular shape. In a possible alternative embodiment, the guide surface 15 and consequently the closed path P may include at least a straight section and at least a curved section. For example, the closed path P may have two straight sections parallel to each other, and two semi-circular sections located at the opposing ends of the two straight sections.

The transfer apparatus 10 comprises a plurality of transfer elements 16. Each transfer element 16 has a gripping surface 17 and is provided with gripping means adapted to hold an article A or a portion of article A on the gripping surface.

The transfer elements 16 are movable on the guide surface 15 of guide element 14 along the closed path P in a mutually independent way.

The guide element 14 is mobile and is associated to moving means 30 configured to move the guide element 14 in such a way that the guide surface 15 moves along the closed path P with a base speed Vb. In the illustrated example, the moving means 30 rotatably move the guide element 14 around a rotation axis C. The guide surface 15 is fixed with respect to the guide element 14, and has a circular shape the axis thereof coincides with the rotation axis C.

In order to move the guide surface 15 along a non-circular closed path P, the guide element 14 may consist of a plurality of sectors which are mutually articulated.

Referring to FIG. 2, the transfer apparatus 10 includes a linear motor 32 comprising a stator 34, which is connected to the guide element 14, and a plurality of movers 36 connected to respective transfer elements 16. The stator 34 of linear motor 32 includes a plurality of electrical windings 38, which are fixed with respect to guide element 14 and are electrically fed by electrical contacts 40 cooperating with a rotating collector 42.

The movers 36 of linear motor 32 include permanent magnets, which are fixed to respective transfer elements 16 and which cooperate with the magnetic field produced by the windings 38 of the stator of linear motor 32.

Linear motor 32 is adapted to move each transfer element 16 along the closed path P with a relative speed Vr with respect to the guide surface 15 of guide element 14. The relative speed Vr of each transfer element 16 may be controlled individually, so that each transfer element 16 moves with respect to guide surface 15 with a specific relative speed Vr, which may be different from the relative speed of the other transfer elements 16.

The linear motor 32 includes a control unit 44, controlling the relative speed Vr of each transfer element along the closed path P. The control unit 44 also controls the moving means 30 which move the guide element with the base speed Vb. The base speed Vb may be constant or may vary, according to a program determined in advance.

Therefore, the guide surface 15 of guide element 14 moves along the closed path P with a base speed Vb which is controlled by the movement means 30, and the transfer elements 16 move on the guide surface 15 along the closed path P with a relative speed Vr with respect to the guide surface 15. Therefore, with respect to a stationary reference system, each transfer element 16 moves along the closed path P with a compound speed Va which is given by the algebraic sum of the base speed Vb and the respective relative speed Vr. The algebraic sum of base speed Vb and relative speed Vr takes into account the orientation of the speed vectors. If speeds Vb and Vr are concordant (going in the same direction), the compound speed Va is the sum of both speeds Vr and Vb. On the other hand, if speeds Vb and Vr are discordant (going in opposite directions) the compound speed Va is given by the difference between speeds Vb and Vr.

Because the transfer elements 16 move on a guide surface 15, which in turn is moving with a base speed Vb, it is possible to increase the compound speed Va with which the transfer elements move along the closed path P.

Referring to FIG. 2, guide element 14 may have the shape of a wheel or a drum, the cylindrical outer surface thereof forming the guide surface 15 whereon the transfer elements 16 are guided. In a possible embodiment, the guide element 14 may have the shape of a circular crown, which carries the guide surface 15 and the windings 38 of linear motor 32 and which is rotatably supported around a stationary hub.

Figure 3:
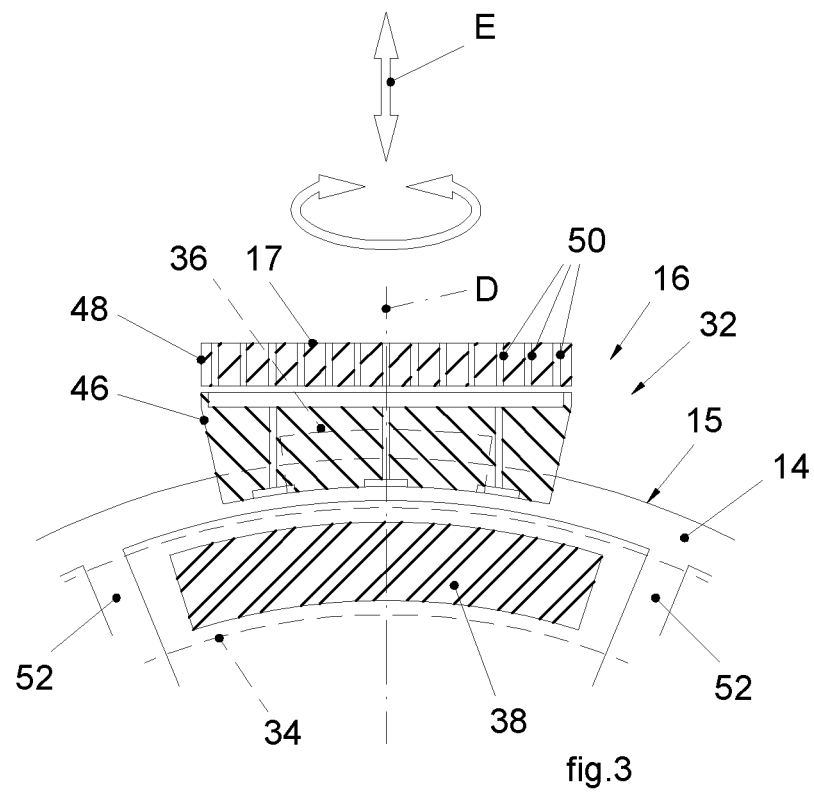
FIG. 3 is a diagrammatic section of an embodiment of a transfer element of an apparatus according to the present invention.

Referring to FIG. 3, at least one of the transfer elements 16 may comprise a base section 36, connected to the mover 36 of linear motor 32, and a movable section 48 which carries at least part of the gripping surface 17.

The movable section 48 of each transfer element 16 may be rotatable with respect to the respective base section 46 around an axis D which is orthogonal to the gripping surface 17. In this way, the gripping elements 16 may perform a rotation of articles A between the pick-up area and the delivery area. In a possible embodiment, the movable section 48 of each transfer element 16 may be translatable with respect to the respective base section 46 along a direction E orthogonal to the gripping surface 17, in such a way as to radially move the gripping surface with respect to the guide surface 15, in order to facilitate the pick-up and release operations of articles A. The rotation and/or translation movements of the movable section 48 with respect to the base section 46 of transfer elements 16 may be controlled via actuators or cam systems.

As shown in FIG. 3, the transfer elements 16 may be provided with suction channels 50 communicating with suction holes, which are opened on the gripping surface 17 to perform suction gripping of articles A. The suction channels 50 may be connected to further suction channels 52 formed in the guide element 14 and opened on the guide surface 15. The suction system is only schematically shown in FIGS. 2 and 3, and may be implemented as described in detail in document EP-A-3336023 by the same Applicant.

As shown in FIG. 3, the gripping surface 17 may be substantially flat. The gripping surface 17 may be orthogonal to a radial axis D which is orthogonal with respect to the rotation axis of guide element 14.

In operation, the movement of the gripping elements 16 along the closed path P may be controlled by the control unit 44 in such a way as to vary the distance between consecutive gripping elements 16 in the path from the pick-up area 12 to the delivery area 13, in such a way as to vary the pitch between articles A in the path from the pick-up area 12 to the delivery area 13 (repitch operation).

Figure 4:
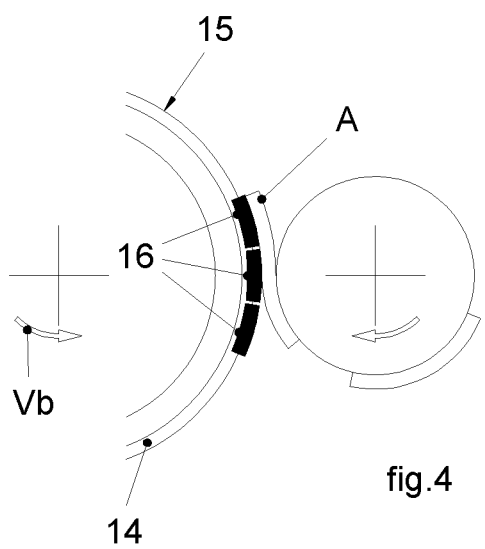
FIGS. 4 and 5 are diagrammatic views which show two operating steps of an apparatus according to the invention.
Figure 5:
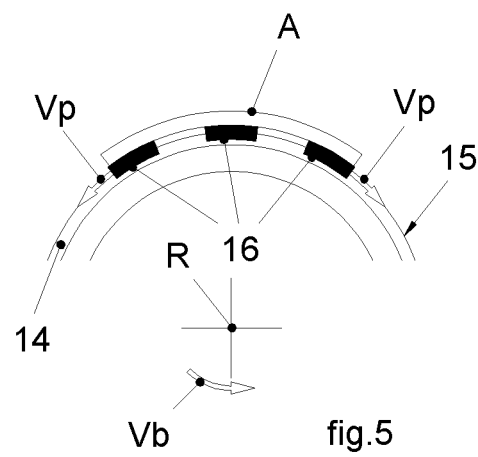

Referring to FIGS. 4 and 5, each article A may be picked up by two or more consecutive transfer elements 16. In the example shown in FIGS. 4 and 5, each article A is picked up by three consecutive transfer elements 16.

As can be seen in a comparison of FIGS. 4 and 5, the distance between consecutive transfer elements 16 holding one and the same article A may be varied along path P in such a way as to stretch articles A. This operation may be useful if articles A are elastic and an elastic stretching operation on articles A is needed before they are applied onto other components.

Of course, without prejudice to the principle of the invention, the implementation details and the embodiments may amply vary with respect to what has been described and illustrated herein, without departing from the extent of protection of the invention as defined in the claims that follow.

The invention claimed is:

1. A transfer apparatus for transferring articles from a pick-up area to a delivery area, comprising:
    a guide element having a guide surface which extends along a closed path which crosses said pick-up area and said delivery area, wherein said guide element is mobile and is associated with a first moving device configured to move said guide element so that the guide surface moves along said closed path at a base speed, and
    a plurality of transfer elements each provided with a gripping surface and with gripping elements configured to hold said article on said gripping surface, wherein each of said plurality of transfer elements is movable with respect to said guide surface along said closed path and is associated with a second moving device for moving each of said plurality of transfer elements along said closed path with a relative speed with respect to the guide surface, so that each of said plurality of transfer elements with respect to a stationary reference system moves along said closed path with a compound speed given by an algebraic sum of said base speed and the respective relative speed.

2. The transfer apparatus of claim 1, wherein said second moving device comprises a linear motor comprising a stator connected to said guide element and a plurality of movers connected to respective transfer elements of the plurality of transfer elements, wherein the linear motor is configured to move each of said plurality of transfer elements along said closed path with said relative speed with respect to the guide surface.

3. The transfer apparatus of claim 2, wherein at least one of said plurality of transfer elements comprises a base section connected to a respective mover and a movable section carrying at least a part of said gripping surface, and wherein said movable section is rotatable with respect to said base section around an axis perpendicular to said gripping surface and/or is translatable with respect to the base section along said axis perpendicular to said gripping surface.

4. The transfer apparatus of claim 1, wherein said guide surface extends along a circular closed path.

5. The transfer apparatus of claim 1, wherein said guide surface extends along the closed path, which comprises at least one straight section and at least one curved section.

6. The transfer apparatus of claim 2, wherein said linear motor comprises a control unit configured to control movement of said plurality of transfer elements and of said guide surface in a coordinated way so that each of said plurality of transfer elements moves along said closed path with a predetermined compound speed.

7. The transfer apparatus of claim 1, wherein said gripping surface is substantially flat.

8. A method for transferring articles from a pick-up area to a delivery area, comprising:
    providing a guide element having a guide surface which extends along a closed path which crosses said pick-up area and said delivery area,
    providing a plurality of transfer elements each provided with a gripping surface and with gripping elements configured to hold an article on said gripping surface, wherein each of said plurality of transfer elements is movable with respect to said guide surface along said closed path,
    moving said guide element by a first moving device so that the guide surface moves along said closed path at a base speed,
    moving each of said plurality of transfer elements by a second moving device along said closed path with a relative speed with respect to the guide surface, so that each of said plurality of transfer elements with respect to a stationary reference system moves along said closed path with a compound speed given by an algebraic sum of said base speed and the respective relative speed.

9. The method of claim 8, comprising varying a distance between at least two consecutive transfer elements of the plurality of transfer elements along said closed path.

10. The method of claim 8, comprising picking up an article by at least two consecutive transfer elements of the plurality of transfer elements.

* * * * *